United States Patent [19]

Gruenfeld

[11] 4,209,514
[45] Jun. 24, 1980

[54] 3-AMINOALKYL-4-ARYL-TETRAHYDROAZEPINES

[75] Inventor: Norbert Gruenfeld, White Plains, N.Y.

[73] Assignee: Ciba-Geigy Corporation, Ardsley, N.Y.

[21] Appl. No.: 963,538

[22] Filed: Nov. 24, 1978

Related U.S. Application Data

[62] Division of Ser. No. 809,840, Jun. 24, 1977, Pat. No. 4,150,129.

[51] Int. Cl.² .................. A61K 31/55; C07D 403/06
[52] U.S. Cl. .................. 424/244; 424/246; 424/248.55; 424/250; 424/267; 424/270; 424/263; 424/272; 424/274; 424/275; 260/239.3 R
[58] Field of Search .................. 260/239.3 R; 424/244, 424/248.55, 246, 250, 267, 272, 270, 274, 275, 263

[56] References Cited

U.S. PATENT DOCUMENTS 4,150,129  4/1979  Gruenfeld ................ 260/239.3 R

OTHER PUBLICATIONS

Chemical Abstracts, vol. 70, item 114,910(x) (1969).
Chemical Abstracts, vol. 74, item 22,522(b) (1971).

Primary Examiner—John M. Ford
Assistant Examiner—Robert T. Bond
Attorney, Agent, or Firm—Theodore O. Groeger

[57] ABSTRACT

3-Aminoalkyl-4-aryl-1,5,6,7-tetrahydro-2H-azepines, e.g. those of the formula

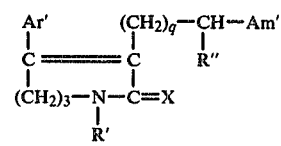

Ar' = phenyl, thienyl, pyridyl or phenyl subst. by alkyl, alkoxy, alkylthio, halo or CF$_3$;
Am' = NH$_2$, (alkyl, alkenyl, alkynyl, hydroxyalkyl, cycloalkyl, or benzyl)amino, its N-lower alkyl derivatives; alkyleneimino, morpholino or piperazino;
q = 0 or 1;
X = H$_2$ or 0;
R', R" = H or alkyl;

and salts thereof are potassium-sparing diuretic agents.

8 Claims, No Drawings

3-AMINOALKYL-4-ARYL-TETRAHYDROAZEPINES

This is a divisional of application Ser. No. 809,840 filed on June 24, 1977, now U.S. Pat. No. 4,150,129.

SUMMARY OF THE INVENTION

The present invention concerns and has for its object the provision of new 3-aminoalkyl-4-aryl-1,5,6,7-tetrahydro-2H-azepines, preferably those corresponding to Formula I

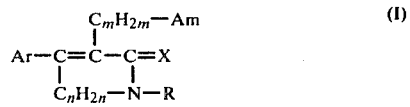

wherein Ar is unsubstituted phenyl, thienyl or pyridyl, or phenyl substituted by up to 3 members selected from lower alkyl, hydroxy, mercapto, lower alkoxy, lower alkylthio, lower alkylenedioxy, halogeno or trifluoromethyl; m is an integer from 1 to 7; $C_nH_{2n}$ is lower alkylene separating the olefinic carbon from the nitrogen atom by 3 carbon atoms; X represents two hydrogens or oxo, R is hydrogen, lower alkyl or hydroxyalkyl and Am is amino, simple or mixed, mono- or di-lower (alkyl, alkenyl, alkynyl, hydroxyalkyl, 3 to 7 ring-membered cycloalkyl or Ar-alkyl)amino; mono- or bicyclic, 5 to 7 ring-membered lower alkyleneimino, or lower mono- (oxa, thia or aza)-alkyleneimino, a lower alkanoyl derivative or a therapeutically useful acid addition salt thereof; as well as of corresponding pharmaceutical compositions and of methods for the preparation and application of these products, which are useful diuretic agents.

DESCRIPTION OF THE PREFERRED EMBODIMENTS

The phenyl radical Ar is preferably phenyl substituted by up to three, especially one or two, of the same or different members selected from the group consisting of lower alkyl, e.g. methyl, ethyl, n- or i-propyl or -butyl; free, etherified or esterified hydroxy or mercapto, such as lower alkoxy, e.g. methoxy, ethoxy, n- or i-propoxy or -butoxy; lower alkylenedioxy, e.g. methylenedioxy or ethylidenedioxy; lower alkylthio, e.g. methylthio or ethylthio; halogeno, e.g. fluoro, chloro or bromo; or trifluoromethyl. Preferred Ar-radicals are phenyl, (hydroxy)phenyl, (lower alkyl)-phenyl, mono- or di-(lower alkoxy)-phenyl, (halogeno)-phenyl or (trifluoromethyl)-phenyl.

The term "lower", referred to above and hereinafter in connection with organic radicals or compounds, respectively, defines such with up to 7, preferably up to 4, carbon atoms.

The radical $C_mH_{2m}$ is preferably ethylene or 1,2-propylene, but may also stand for methylene, 1,3-propylene, 1,2-, 1,3- or 1,4-butylene, 1,2-, 1,3- or 1,4-pentylene, -hexylene or -heptylene.

The lower alkylene radical $C_nH_{2n}$ is preferably 1,3-propylene, but also represents 1,3-butylene, 1,3- or 2,4-pentylene.

An open or cyclic amino group Am is exemplified by amino, lower (alkyl, alkenyl, alkynyl or hydroxyalkyl)amino, e.g. (methyl, ethyl, n- or i-propyl, -butyl, -pentyl, -hexyl or -heptyl; allyl, 2- or 3-butenyl; propargyl, 2- or 3-butynyl; or 2-hydroxyethyl, 2- or 3-hydroxypropyl)amino; (3 to 7 ring-membered cycloalkyl or Ar-lower alkyl)amino, e.g. (cyclopentyl, cyclohexyl; benzyl or phenethyl)amino; or the N-lower alkyl-derivatives of said sec. amino groups, e.g. the N-(methyl, ethyl, n- or i-propyl, -butyl, -pentyl, -hexyl or -heptyl)-derivatives thereof; 5 to 7 ring-membered mono- or bicyclic lower alkyleneimino, e.g. pyrrolidino, piperidino, (1,4-, 1,5-, 1,6-, 2,5-, 2,6- or 1,7-hexylene or -heptylene)imino; 2- or 3-azabicyclo[3.2.2]nonyl or [4.3.1]decyl; or lower mono-oxa, thia or aza-alkyleneimino, e.g. morpholino, thiamorpholino, piperazino or N-(lower alkyl or hydroxyalkyl)-piperazino, e.g. N-(methyl, ethyl or 2-hydroxyethyl)-piperazino.

The radical X is preferably oxo and R advantageously hydrogen, but also lower alkyl or hydroxyalkyl, preferably methyl, ethyl, hydroxymethyl or 2-hydroxyethyl.

The lower alkanoyl derivatives of said compounds of Formula I are preferably those containing alkanoyl attached to a primary or secondary amino group Am, and/or those wherein $X=H_2$ and $R=H$; e.g. the acetyl, propionyl or pivaloyl derivatives.

Salts of the compounds of Formula I are preferably addition salts of the therapeutically useful inorganic or organic acids listed below.

The compounds of the invention exhibit valuable pharmacological properties. Primarily they show diuretic, natri- and chloroiuretic activity with rapid onset of action, high urine but low potassium excretion levels. This can be demonstrated in animal tests using, for example mammals, e.g. rats or dogs, as test objects. Such tests are performed, for example, by administering the compounds of the invention within a gelatin capsule to dogs, or in the form of aqueous solutions or starchy suspensions by stomach tube to rats, in an oral dosage range between about 0.5 and 100 mg/kg/day, preferably between about 1 and 50 mg/kg/day, advantageously between about 5 and 25 mg/kg/day. Simultaneously the test animals may receive various salt loads enterally or parenterally, for example various amounts of subcutaneously applied 0.9% saline, e.g. 100 ml thereof per medium-sized dog (beagle). Urine is then collected, e.g. at 2 hour intervals, with or without catheterization, and its volume, sodium, potassium and chloride content estimated and compared with that of the same untreated or saline-treated animals. Besides the anti-edematous utility, the compounds of the invention can also be used as intermediates in the preparation of other valuable products, primarily of pharmacologically active compounds or compositions, e.g. as components of antihypertensive agents.

Preferred and highly diuretic are those compounds of Formula I in which Ar is phenyl, (lower alkyl)-phenyl, mono- or di-(lower alkoxy)-phenyl, (lower alkylthio)-phenyl, (halogeno)-phenyl or (trifluoromethyl)-phenyl, m is an integer from 1 to 7, $C_nH_{2n}$ is 1,3-propylene or 1,3-butylene, X represents two hydrogens or oxo, R is hydrogen, lower alkyl or hydroxyalkyl and Am is amino, lower (alkyl, alkenyl, alkynyl, hydroxyalkyl, 5 or 6 ring-membered cycloalkyl or phenyl-lower alkyl)amino, the N- lower alkyl-derivatives of said sec. amino groups; 5 to 7 ring-membered lower alkyleneimino,morpholino, thiamorpholino, piperazino or N-(lower alkyl or hydroxyalkyl)-piperazino; the lower alkanoyl derivatives of said compounds wherein Am is prim. or sec. amino or both X and R are hydrogen; or a therapeutically useful acid addition salt thereof.

Especially valuable and suitable for said utility are compounds of Formula II

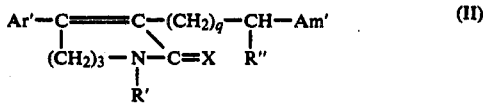

wherein Ar' is phenyl, (alkyl)-phenyl, mono- or di-(alkoxy)-phenyl or (alkylthio)-phenyl wherein the alkyl contains up to 4 carbon atoms, (halogeno)-phenyl or (trifluoromethyl)-phenyl, Am' is amino, lower (alkyl, alkenyl, alkynyl, hydroxyalkyl, 5 or 6 ring-membered cycloalkyl or benzyl)amino, the N-lower alkyl derivatives of said sec. amino groups, 5 to 7 ring-membered lower alkyleneimino, morpholino, thiamorpholino, piperazino or N-lower alkyl-piperazino; X represents two hydrogens or oxo; each of R' and R" is hydrogen or alkyl with up to 4 carbon atoms and q is the integer 0 or 1; or a therapeutically useful acid addition salt thereof.

More preferred are compounds of Formula II, wherein Ar' is phenyl, tolyl, mono- or dimethoxyphenyl, methylthiophenyl, fluorophenyl, chlorophenyl or trifluoromethylphenyl; Am' is amino, (methyl, ethyl, n- or i-propyl, allyl, propargyl, 2-hydroxyethyl, cyclopentyl, cyclohexyl or benzyl)amino, or the N-(methyl, ethyl, n- or i-propyl, -butyl, -pentyl, -hexyl or -heptyl)-derivatives of said sec. amino groups; pyrrolidino, piperidino, morpholino or N-methylpiperazino; X is oxo; each of R' and R" is hydrogen or methyl and q is one; or a therapeutically useful acid addition salt thereof.

Outstanding are compounds of Formula II, wherein Ar' is m- or p-methoxyphenyl, Am' is N-(methyl, ethyl, n- or i-propyl, allyl or propargyl)-N-(methyl, ethyl, i-propyl or n-butyl)amino; pyrrolidino, piperidino or morpholino; X is oxo, R' is hydrogen or methyl, R" is methyl and q is one; or a therapeutically useful acid addition salt thereof which, when given to rats or dogs at oral doses as low as 1.25–10 mg/kg/day, exhibit marked diuretic, natri- and chloriuretic effects.

The compounds of the invention are prepared according to methods in themselves known. Advantageously they are obtained by: (a) reducing Schiff's bases or oximes obtained from compounds of Formula III

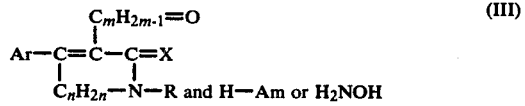

$C_nH_{2n}-N-R$ and H—Am or H$_2$NOH or reducing nitriles or amides of Formula IV

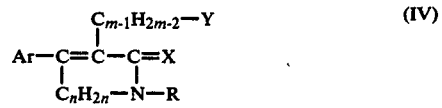

wherein Y is CN or COAm and, if desired, converting any resulting compound into another compound of the invention.

Said reduction is carried out according to known methods, for example with the use of hydrogen in the presence of catalysts, e.g. platinum or nickel catalysts, or with nascent hydrogen, e.g. generated electrolytically, advantageously in case of said Schiff's bases or oximes. Also reducing agents are useful for both of said ketone- or acid-derived starting materials, preferably simple or complex light metal hydrides, such as lithium aluminum hydride, alane, boranes or sodium cyanoborohydride under appropriate conditions to either preserve a carbonyl group in 2-position; i.e. to preserve X=O, or convert X=O to X=H$_2$.

The starting material is new and compounds of Formula III exhibit valuable pharmacological properties also, for example antiallergic effects, as can be demonstrated in the passive cutaneous anaphylaxis test according to J. Carr; J. Path. 108, 1 (1972). They are preferably prepared by adding 2-Ar-1-pyrrolines to butenolides, preferably α-angelicalactone (for compounds of Formula II), either in the absence or presence of diluents, such as hydrocarbons or esters, e.g. toluene, xylene or ethyl acetate, advantageously at elevated temperatures, e.g. between 80° and 140°. Said nitriles or amides of Formula IV are advantageously prepared from those of Formula II wherein Am' is monoalkylamino by reaction with butyl lithium, followed by cyanogen bromide or carbon dioxide and amidizing the resulting acid with HAm and diimidazolylcarbonyl.

Another process for preparing the compounds of the invention consists in condensing reaction esters of Formula V

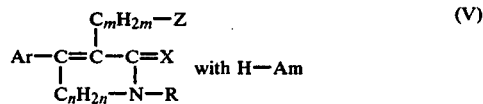

wherein Z is a reactively esterified hydroxy group, for example, such esterified by a strong inorganic or organic acid, above all a hydrohalic acid, e.g. hydrochloric, hydrobromic or hydriodic acid; sulfuric or an aromatic sulfonic acid, e.g. p-toluene or m-bromobenzene sulfonic acid. Said condensation is preferably carried out in the presence or absence of a basic agent, such as an alkali or alkaline earth metal hydroxide, carbonate or bicarbonate, e.g. sodium, potassium or calcium hydroxide or carbonate; alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine.

The starting material of Formula V can be prepared by reducing the compounds of Formula III to the corresponding alcohols, e.g. with sodium borohydride, and reactively esterifying them with said inorganic or organic acids, or reactive derivatives thereof, e.g. phosphorus trihalides or sulfonyl halides. Variously compounds of Formula V, wherein Z is hydrogen and m is 1, can be lithiated, e.g. with n-butyl lithium, and reacted with lower alkyl disulfides, to yield compounds V with Z being lower alkylthio. These, in turn, can be converted into those with Z being halogen, by cleaving them with sulfuryl halides; e.g. sulfuryl chloride.

The compounds of the invention thus obtained can be converted into each other according to conventional methods. For example, resulting phenolethers may be hydrolyzed with hydrobromic acid or boron tribromide, or prim. or sec. amines reacted with reactive esters of the respective alcohols, preferably derived from hydrohalic, aliphatic or aromatic sulfonic acids, e.g. lower alkyl sulfonates, e.g. the mesylate or tosylate, or with corresponding aldehydes or ketones and reducing agents, e.g. formic acid or sodium cyanoborohydride, in order to obtain sec. or tert. amines, respectively. Acyl-derivatives of prim. or sec. amines are obtained by conventional acylation with reactive acid derivatives, e.g. anhydrides or halides. Resulting acyl derivatives, or compounds of Formula I with X=O, can be reduced as shown for the amides of Formula IV, e.g. mildly with said simple hydrides, such as alane or boranes in order to retain X=O, or with stronger complex metal hydrides, e.g. lithium aluminum hydride, in order to obtain compounds with X=H$_2$.

Finally, a resulting base can be converted into a corresponding acid addition salt, preferably with the use of a therapeutically acceptable acid or anion exchange preparation; or resulting salts can be converted into the corresponding free bases, for example, with the use of a base, such as a metal hydroxide, basic salt, ammonia, amine or cation exchange preparation, e.g. an alkali metal hydroxide or carbonate. Said acid addition salts are preferably such of therapeutically useful inorganic acids, such as strong metalloidic acids, for example, hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyruvic, phenylacetic benzoic, 4-aminobenzoic, anthranilic, 4-hydroxybenzoic, salicylic, embonic, nicotinic; methanesulfonic, ethanesulfonic, hydroxyethanesulfonic, benzenesulfonic, halogen-benzenesulfonic, toluenesulfonic, naphthalenesulfonic, sulfanilic or cyclohexylsulfamic acid.

These or other salts, for example, the picrates or tetrafluoroborates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances. Resulting mixtures of isomers, e.g. diastereo or optical isomers, can be separated into the single isomers by methods in themselves known, e.g. by fractional distillation, crystallization and/or chromatography, or separation of diastereomeric salts. As is obvious from Formula II, the carbon atom in the CHAm'-moiety (R" is not hydrogen) is an asymmetric carbon atom, yielding racemates.

The invention further includes any variant of the present process in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts. Mainly those starting materials should be used in the reactions of the invention that lead to the formation of those compounds indicated above as being especially valuable.

The above reactions are carried out according to standard methods, in the presence or absence of diluents, preferably such as are inert to the reagents are are solvents thereof of catalysts, condensing or neutralizing agents and/or inert atmospheres, at low temperatures, room temperature or advantageously elevated temperatures, at atmospheric or superatmospheric pressure.

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinyl-pyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promotors, salts for regulating the osmotic pressure and/or buffers. They may also contain other therapeutically valuable substances. Said pharmaceutical compositions are parpared according to conventional mixing, granulating or coating methods respectively and contain about 0.1 to 75%, preferably about 1 to 50% of the active ingredient.

The following examples, illustrating the invention, are not to be construed as being limitations thereon. Temperatures are given in degrees Centigrade and all parts wherever given are parts by weight. If not mentioned otherwise, all evaporations are performed under reduced pressure, e.g. between about 15 and 100 mmHg.

EXAMPLE 1

The solution of 8.0 g of 3-acetonyl-4-(3-methoxyphenyl)-1,5,6,7-tetrahydro-2H-azepinone, 14.95 g of piperidine, 6.6 ml of 5 N methanolic hydrogen chloride and 1.9 g of sodium cyanoborohydride in 120 ml of methanol is refluxed overnight. An additional portion of 0.95 g of sodium cyanoborohydride is added and refluxing continued for 24 hours. The mixture is cooled to 0°, 30 ml of concentrated hydrochloric acid are added and the solution concentrated. The concentrate is diluted with 100 ml of water, the solution washed with benzene and rendered basic with 70 ml of 3 N aqueous sodium hydroxide. It is extracted with diethyl ether, the extract evaporated and the residue crystallized from petroleum ether and hexane, to yield the 3-(2-piperidinopropyl)-4-(3-methoxyphenyl)-1,5,6,7-tetrahydro-2H-azepinone of the formula

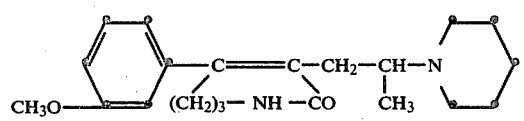

melting at 97° to 99°.

The starting material is prepared as follows: The solution of 70 g of 2-(3-methoxyphenyl)-1-pyrroline [J. Org. Chem. 23, 1278, 1281 (1958)] and 43.2 g of α-angelicalactone in 600 ml of toluene is refluxed overnight. A second portion of 43.2 g of α-angelicalactone is added, the mixture is again refluxed overnight, cooled and evaporated. The residue is crystallized from 50 ml of ethyl acetate, to yield the 3-acetonyl-4-(3-methoxyphenyl)-1,5,6,7-tetrahydro-2H-azepinone, melting at 140°–142°.

EXAMPLE 2

The solution of 1.36 g of 3-acetonyl-4-(3-methoxyphenyl)-1,5,6,7-tetrahydro-2H-azepinone, 0.52 g of pyrrolidine and 0.1 g of p-toluenesulfonic acid hydrate in 10 ml of benzene is refluxed with water separation for 4 hours and evaporated. The residue is dissolved in 15 ml of ethanol and the solution hydrogenated over 0.1 g of platinum oxide at atmospheric pressure and room temperature. The mixture is filtered, the filtrate evaporated and the resulting oil dissolved in 2 N hydrochloric acid. The solution is washed with benzene, basified with 3 N aqueous sodium hydroxide and extracted with diethyl ether. The extract is dried, evaporated and the residue recrystallized from petroleum ether and hexane, to yield the 3-(2-pyrrolidinopropyl)-4-(3-methoxyphenyl)-1,5,6,7-tetrahydro-2H-azepinone melting at 94° to 96°.

EXAMPLE 3

The solution of 1.3 g of 3-(2-hydroxyiminopropyl)-4-(3-methoxyphenyl)-1,5,6,7-tetrahydro-2H-azepinone in 60 ml of ethanol is hydrogenated in the presence of 0.5 g of Raney nickel at room temperature and atmospheric pressure. It is filtered, the filtrate evaporated the residue treated with about 2 ml of ethanolic hydrochloric acid, crystallized from ethanol-acetone and recrystallized from ethanol, to yield the 3-(2-aminopropyl)-4-(3-methoxyphenyl)-1,5,6,7-tetrahydro-2H-azepinone hydrochloride melting at 217°–219°.

The starting material is prepared as follows: The mixture of 7.0 g of 3-acetonyl-4-(3-methoxyphenyl)-1,5,6,7-tetrahydro-2H-azepinone, 3.88 g of potassium carbonate, 3.55 g of hydroxylamine hydrochloride, 5 ml of water and 60 ml of methanol is refluxed for 5 hours and then stirred at room temperature overnight. 80 ml of water are added, the precipitate collected and washed with ethanol and diethyl ether, to yield the 3-(2-hydroxyiminopropyl)-4-(3-methoxyphenyl)-1,5,6,7-tetrahydro-2H-azepinone, melting at 155°–158°.

EXAMPLE 4

The solution of 8.0 g of 1-methyl-3-acetonyl-4-(3-methoxyphenyl)-1,5,6,7-tetrahydro-2H-azepinone, 14.2 g of piperidine, 6.4 ml of 5 N methanolic hydrogen chloride and 1.91 g of sodium cyanoborohydride in 100 ml of methanol is refluxed overnight. An additional portion of 1.91 g of sodium cyanoborohydride is added and refluxing continued for another day. The solution is cooled, acidified with 35 ml of concentrated hydrochloric acid and evaporated. The residue is diluted with 100 ml of water, the aqueous solution washed with benzene, filtered, basified with 65 ml 3 N aqueous sodium hydroxide and extracted with diethyl ether. The extract is dried, evaporated and the residue crystallized from petroleum ether and recrystallized from hexane, to yield the 1-methyl-3-(2-piperidinopropyl)-4-(3-methoxyphenyl)-1,5,6,7-tetrahydro-2H-azepinone melting at 101°–103°.

The starting material is prepared as follows: The solution of 27.2 g of 3-acetonyl-4-(3-methoxyphenyl)-1,5,6,7-tetrahydro-2H-azepinone, 31 g of ethylene glycol and 0.2 g of p-toluene-sulfonic acid hydrate in 200 ml of benzene is refluxed with a water separator for 7 hours. It is cooled to 0°, 100 ml of 5% aqueous sodium bicarbonate are added and the benzene layer separated. It is washed with water, dried, evaporated and the residue crystallized from diethyl ether to give the 3-(2-ethylenedioxypropyl)-4-(3-methoxyphenyl)-1,5,6,7-tetrahydro-2H-azepinone melting at 132°–134°.

To the solution of 27.0 g thereof in 110 ml of dimethylformamide, 5.4 g of a 57% suspension of sodium hydride in mineral oil are added and the mixture is stirred at room temperature for 2 hours. The solution of 28.4 ml of methyl iodide in 20 ml of dimethylformamide is added dropwise at room temperature and the mixture stirred at room temperature overnight. It is poured onto 500 g of ice, the precipitate collected and washed with water, to yield the 1-methyl-3-(2-ethylenedioxypropyl)-4-(3-methoxyphenyl)-1,5,6,7-tetrahydro-2H-azepinone melting at 113°–115°.

The suspension of 20 g thereof in a mixture of 150 ml of ethanol and 150 ml of 0.2 N hydrochloric acid is stirred at room temperature for 3 days. It is concentrated at room temperature, the separated oil extracted with chloroform, the extract dried and evaporated, to give the 1-methyl-3-acetonyl-4-(3-methoxyphenyl)-1,5,6,7,-tetrahydro-2H-azepinone showing an I.R.-band at 1700 cm$^{-1}$.

EXAMPLE 5

The solution of 15.1 g of 3-acetonyl-4-(3,4-dimethoxyphenyl)-1,5,6,7-tetrahydro-2H-azepinone, 25.5 ml of isopropylamine 10 ml of 5.8 N methanolic hydrogen chloride and 3.4 g of sodium cyanoborohydride in 260 ml of methanol is refluxed for 3 days. The mixture is cooled, acidified to pH=1 with concentrated hydrochloric acid, evaporated and the residue diluted with water. It is washed with ether, basified with 3 N aqueous sodium hydroxide to pH=11 and extracted with diethyl ether. The extract is dried, evaporated and the residue dissolved in 75 ml of acetone. The solution is treated with 4.4 N ethanolic hydrogen chloride, and the precipitate collected, to yield the 3-(2-isopropylaminopropyl)-4-(3,4-dimethoxyphenyl)-1,5,6,7-tetrahydro-2H-azepinone hydrochloride monohydrate melting at 135°–138°.

The starting material is prepared as shown in Example 1, it melts at 137°–140°.

EXAMPLE 6

The mixture of 22.1 g of 3-(2-piperidinopropyl)-4-(4-methoxyphenyl)-1,5,6,7-tetrahydro-2H-azepinone and 128 ml of 48% hydrobromic acid is stirred under reflux for six hours. It is cooled, basified with concentrated ammonia and extracted with chloroform. The extract is dried, evaporated, the residue crystallized from diethyl ether and recrystallized from acetone, to yield the 3-(2-piperidinopropyl)4-(4-hydroxyphenyl)-1,5,6,7-tetrahydro-2H-azepinone melting at 178°–181°.

EXAMPLE 7

The solution of 1.0 g of 3-(2-hydroxyiminopropyl)-4-(3-methoxyphenyl)-1,5,6,7-tetrahydro-2H-azepinone (Example 3) in 10 ml of tetrahydrofuran is treated with 8.7 ml of Molar alanetriethylamine in benzene while stirring at 0° C. After 2 hours the mixture is stirred at room temperature overnight and subsequently refluxed for 3 hours after addition of 10 ml of benzene. The mixture is again cooled in an ice bath, treated first with 5 ml of water, then 5 ml of 3 N aqueous sodium hydroxide and the organic layer is separated. The aqueous solution is extracted with benzene, the combined organic layer is dried, evaporated and the residue is dissolved in 10 ml of 6 N hydrochloric acid. The solution is washed with benzene, basified with 3 N aqueous sodium hydroxide and extracted with methylene chloride. The extract is evaporated, the residue dissolved in diethyl ether and 0.45 ml of 8 N ethanolic hydrogen chloride are added. The resulting solid is collected and recrystallized from acetone-ethanol, to give 3-(2-aminopropyl)-4-(3-methoxyphenyl)-1,5,6,7-tetrahydro-2H-azepine dihydrochloride melting at 246°–248° C.

EXAMPLE 8

The solution of 13.6 g of 3-acetonyl-4-(4-methoxyphenyl)-1,5,6,7-tetrahydro-2H-azepinone, 25.5 ml of isopropylamine, 10 ml of 5.8 N methanolic hydrogen chloride and 3.4 g of sodium cyanoborohydride in 260 ml of methanol is refluxed for three days. The mixture is cooled to 0°, acidified to pH=1 with concentrated hydrochloric acid and evaporated. The residue is taken up in water, the mixture washed with diethyl ether, rendered basic to pH=10–11 with 3 N aqueous sodium hydroxide and extracted with diethyl ether. The extract is dried, evaporated and 13.5 g of the residual free base is dissolved in 80 ml of acetone. The solution is treated with 10.5 ml of 4.4 N ethanolic hydrochloric acid, the mixture evaporated, the residue crystallized from diethyl ether and recrystallized from isopropanol-ethyl acetate, to yield the 3-(2-isopropylaminopropyl)-4-(4-methoxyphenyl)-1,5,6,7-tetrahydro-2H-azepinone hydrochloride hemihydrate melting at 165°–167°.

The 3-(2-isopropylaminopropyl)-4-(3-methoxyphenyl)-1,5,6,7-tetrahydro-2H-azepinone is similarly prepared. It shows major I.R.-bands at 1650, 3150 and 3350 cm$^{-1}$ (in chloroform).

EXAMPLE 9

4.78 ml of glacial acetic acid are added dropwise to the ice-cooled mixture of 7.6 g of 3-(2-isopropylaminopropyl)-4-(4-methoxyphenyl)-1,5,6,7-tetrahydro-2H-azepinone, 13.3 ml of acetaldehyde, 4.5 g of sodium cyanoborohydride and 90 ml of acetonitrile. The mixture is stirred at room temperature for 90 minutes, cooled in an ice-bath, acidified to pH=1 with concentrated hydrochloric acid and evaporated. The residue is taken up in 150 ml of water, the solution washed with diethyl ether, filtered, basified with 3 N aqueous sodium hydroxide and extracted with diethyl ether. The extract is dried, evaporated, the residue crystallized from petroleum ether and further purified by suspension in hexane, to yield the 3-[2-(N-isopropyl-N-ethylamino)-propyl]-4-(4-methoxyphenyl)-1,5,6,7-tetrahydro-2H-azepinone melting at 64°–66°.

Similarly prepared is the 3-[2-(N-isopropyl-N-ethylamino)-propyl]-4-(3-methoxyphenyl)-1,5,6,7-tetrahydro-2H-azepinone melting at 86°–88°.

By substituting propionaldehyde for acetaldehyde one obtains the 3-[2-(N-isopropyl-N-n-propylamino)-propyl]-4-(4-methoxyphenyl)-1,5,6,7-tetrahydro-2H-azepinone melting at 90°–92°.

EXAMPLE 10

The mixture of 6.3 g of 3-(2-isopropylaminopropyl)-4-(4-methoxyphenyl)-1,5,6,7-tetrahydro-2H-azepinone, 20 ml of ethylene oxide and 25 ml of absolute ethanol is stirred in a sealed vessel at room temperature for 5 days. The resulting solution is evaporated, the residue crystallized from petrolem ether and recrystallized from ethyl acetate-hexane, to yield the 3-[2-(N-isopropyl-N-hydroxyethylamino)-propyl]-4-(4-methoxyphenyl)-1,5,6,7-tetrahydro-2H-azepinone melting at 109°–111°.

EXAMPLE 11

The mixture of 8.23 g of 3-(2-isopropylaminopropyl)-4-(4-methoxyphenyl)-1,5,6,7-tetrahydro-2H-azepinone, 2.25 ml of methyl iodide, 3.59 g of potassium carbonate and 100 ml of absolute ethanol is refluxed for five hours and evaporated. The residue is suspended in 100 ml of water and the suspension extracted with diethyl ether. The extract is dried, evaporated and the residue crystallized from ethanol-water to yield the 3-[2-(N-isopropyl-N-methylamino)-propyl]-4-(4-methoxyphenyl)-1,5,6,7-tetrahydro-2H-azepinone melting at 86°–88°.

Starting with allyl bromide, the 3-[2-(N-isopropyl-N-allylamino)-propyl]-4-(4-methoxyphenyl)-1,5,6,7-tetrahydro-2H-azepinone is prepared in analogous fashion; it melts at 95°–97°.

EXAMPLE 12

The solution of 6.5 g of 3-(2-methoxyiminopropyl)-4-(4-methoxyphenyl)-1,5,6,7-tetrahydro-2H-azepinone in 150 ml of ethanol is hydrogenated at room temperature and atmospheric pressure in the presence of 10 g of Raney nickel until the uptake of 2 mole equivalents of hydrogen is complete. The mixture is filtered, the filtrate evaporated and the residue dissolved in 100 ml of water and 10 ml of 6 N hydrochloric acid. The acidic solution is washed with diethyl ether, filtered, basified with 30 ml of 3 N aqueous sodium hydroxide and repeatedly extracted with chloroform. The extract is dried, evaporated and the residue is purified by suspension in diethyl ether, to give the 3-(2-aminopropyl)-4-(4-methoxyphenyl)-1,5,6,7-tetrahydro-2H-azepinone melting at 131°–133°.

The starting material is prepared as follows: 2.8 g of methoxyamine hydrochloride are added to the solution of 9.1 g of 3-acetonyl-4-(4-methoxyphenyl)-1,5,6,7-tetrahydro-2H-azepinone in a mixture of 200 ml of absolute ethanol and 100 ml of pyridine. The solution is stirred at room temperature overnight and poured into 3000 ml of ice-water. The mixture is stirred for two hours, the resulting precipitate collected and dried, to yield said O-methyloxime melting at 121°–123°.

EXAMPLE 13

The solution of 6.15 g of 3-(2-piperidinopropyl)-4-(3-methoxyphenyl)-1,5,6,7-tetrahydro-2H-azepinone in 60 ml of methylene chloride, cooled in a dry ice-acetone bath, is added slowly to 120 ml of a similarly precooled 10% solution of boron tribromide in methylene chloride. The mixture is allowed to warm to room temperature and stirred for four hours. It is again cooled in an ice bath, 120 ml of 3 N aqueous sodium hydroxide are added and stirring at room temperature is continued for 30 minutes. The aqueous layer is separated and the methylene chloride solution is washed with 60 ml of water. The combined aqueous solution is neutralized to pH=9–10 with 6 N hydrochloric acid and the precipitate collected, to yield the 3-(2-piperidinopropyl)-4-(3-hydroxyphenyl)-1,5,6,7-tetrahydro-2H-azepinone melting at 218°–220°.

EXAMPLE 14

According to the methods illustrated by the previous examples, the following compounds of Formula II are prepared from equivalent amounts of the corresponding starting materials: R″=CH$_3$, X=O and q=1:

| No. | Ar' | Am' | R' | Salt | m.p. °C. |
|---|---|---|---|---|---|
| 1 | phenyl | isopropylamino | H | — | 95-7 |
| 2 | " | dimethylamino | H | — | 145-7 |
| 3 | " | piperidino | H | — | 143-5 |
| 4 | " | morpholino | H | — | 138-0 |
| 5 | 4-$CH_3$—$C_6H_4$ | piperidino | H | — | 136-8 |
| 6 | 2-$CH_3O$—$C_6H_4$ | " | H | HCl . ½ $H_2O$ | 168-0 |
| 7 | 3-$CH_3O$—$C_6H_4$ | dimethylamino | H | — | 110-2 |
| 8 | " | " | $CH_3$ | HCl | 150-2 |
| 9 | " | 4-$CH_3$-piperidino | H | — | 125-7 |
| 10 | " | 3,5-$(CH_3)_2$-piperidino | H | — | 133-5 |
| 11 | " | | H | — | 103-5 |
| 12 | " | N—$(CH_2)_6$ (bicyclic N structure) | H | — | 109-1 |
| 13 | 3-$CH_3$-4-$CH_3O$—$C_6H_3$ | isopropylamino | H | — | 85-8 |
| 14 | 4-$CH_3O$—$C_6H_4$ | dimethylamino | H | — | 116-8 |
| 15 | " | piperidino | H | — | 115-8 |
| 16 | 4-F—$C_6H_4$ | dimethylamino | H | — | 140-2 |
| 17 | " | piperidino | H | — | 142-4 |
| 18 | 4-Cl—$C_6H_4$ | dimethylamino | H | — | 145-6 |
| 19 | " | isopropylamino | H | — | 117-9 |
| 20 | " | cyclohexylamino | H | — | 148-0 |
| 21 | " | piperidino | H | — | 144-6 |
| 22 | 3,4-$(CH_3O)_2$—$C_6H_3$ | isopropylamino | H | HCl . $H_2O$ | 135-8 |
| 23 | " | dimethylamino | H | — | 68-0 |
| 24 | 3-Cl-4-$CH_3O$—$C_6H_3$ | piperidino | H | — | 164-6 |
| 25 | " | diethylamino | H | — | 107-9 |
| 26 | 4-HO—$C_6H_4$ | piperidino | H | — | 178-1 |
| 27 | 2-thienyl | " | H | — | 133-5 |
| 28 | 3-pyridyl | " | H | — | 159-1 |
| 29 | 2-thienyl | $C_2H_5$—N—$CH(CH_3)_2$ | H | — | 76-8 |
| 30 | 4-$CH_3O$—$C_6H_4$ | " | H | — | 64-6 |
| 31 | " | " | $CH_3$ | — | 69-1 |
| 32 | " | $N(C_2H_5)_2$ | H | — | 111-3 |
| 33 | " | $N(nC_3H_7)_2$ | H | — | 87-9 |
| 34 | " | $CH_3$—N—$C_2H_5$ | H | — | 97-9 |
| 35 | " | $CH_3$—N—$CH(CH_3)_2$ | H | — | 86-8 |
| 36 | " | 4-$CH_3$-piperazino | H | — | 148-0 |

The ketonic starting materials are new and are prepared as illustrated by Example 1. Following are the melting points of said ketones yielding the above-numbered final products: No. 1–4 160°–3°; 5: 162°–4°; 6: 153°–5°; 7–12: 140°–2°; 1–15: 156°–9°; 16,17: 138°–0°; 18–21: 122°–6°; 22,23: 137°–0°; 24,25: 139°–1°; 26: 189°–1°; 27: 139°–1°; 28: 116°–9°; 13: 157°–9°.

EXAMPLE 15

Preparation of 10,000 tablets each containing 100.0 mg of the active ingredient:

Formula

| | |
|---|---|
| 3-[2-(N-ethyl-N-isopropylamino)-propyl]-4-(4-methoxyphenyl)-1,5,6,7-tetrahydro-2H-azepinone | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

Preparation of 10,000 capsules each containing 50.0 mg of the active ingredient:

Formula

| | |
|---|---|
| 3-[2-(N-ethyl-N-isopropylamino)-propyl]-4-(4-methoxyphenyl)-1,5,6,7-tetrahydro-2H-azepinone | 500.0 g |
| Lactose | 2,350.0 g |
| Talcum powder | 150.0 g |

Procedure

All the powders are passed through a screen with openings of 0.6 mm. Then the drug substance is placed in a suitable mixer and mixed first with the talcum, then with the lactose until homogenous. No. 2 capsules are filled with 300 mg of the mixture, using a capsule filling machine.

Analogously, tablets and capsules are prepared from the other compounds illustrated in the previous examples.

I claim:
1. A 3-aminoalkyl-4-aryl-1,5,6,7-tetrahydro-2H-azepinone of the formula

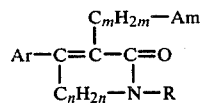

wherein Ar is unsubstituted phenyl, thienyl or pyridyl, or phenyl substituted by up to 3 members selected from lower alkyl, hydroxy, mercapto, lower alkoxy, lower alkylthio, lower alkylenedioxy, halogeno or trifluoromethyl; m is an integer from 1 to 7; $C_n H_{2n}$ is lower alkylene separating the olefinic carbon from the nitrogen atom by 3 carbon atoms; R is hydrogen, lower alkyl or lower hydroxyalkyl and Am is mono- or bi-cyclic, 5 to 7 ring-membered lower alkyleneimino, or lower mono- (oxa, thia or aza)alkyleneimino, a lower alkanoyl derivative of said compounds wherein R is hydrogen, or a therapeutically useful acid addition salt thereof.

2. A compound as claimed in claim 1, in which formula Ar is phenyl, (lower alkyl)-phenyl, mono- or di-(lower alkoxy)-phenyl, (lower alkylthio)-phenyl, (halogeno)-phenyl or (trifluoromethyl)-phenyl, m is an integer from 1 to 7, $C_nH_{2n}$ is 1,3-propylene or 1,3-butylene, R is hydrogen, lower alkyl or lower hydroxyalkyl and Am is 5 to 7 ring-membered lower alkyleneimino, morpholino, thiamorpholino, piperazino or N-(lower alkyl or hydroxyalkyl)-piperazino; the lower alkanoyl derivatives of said compounds wherein R is hydrogen; or a therapeutically useful acid addition salt thereof.

3. A compound as claimed in claim 1, and corresponding to the formula

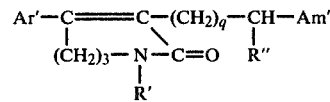

wherein Ar' is phenyl, (alkyl)-phenyl, mono- or di-(alkoxy)phenyl or (alkylthio)-phenyl, wherein the alkyl contains up to 4 carbon atoms, (halogeno)-phenyl or (trifluoromethyl)-phenyl); Am' is 5 to 7 ring-membered lower alkyleneimino, morpholino, thiamorpholino, piperazino or N-lower alkyl-piperazino; each of R' and R'' is hydrogen or alkyl with up to 4 carbon atoms and q is the integer 0 or 1; or a therapeutically useful acid addition salt thereof.

4. A compound as claimed in claim 3, in which formula Ar' is phenyl, tolyl, mono- or dimethoxyphenyl, methylthiophenyl, fluorophenyl, chlorophenyl or trifluoromethylphenyl; Am' is pyrrolidino, piperidino, morpholino or N-methylpiperazino; each of R' and R'' is hydrogen or methyl and q is one; or a therapeutically useful acid addition salt thereof.

5. A compound as claimed in claim 3, in which formula Ar' is m- or p-methoxyphenyl, Am' is; pyrrolidino, piperidino or morpholino; X is oxo, R' hydrogen or methyl, R'' is methyl and q is one; or a therapeutically useful acid addition salt thereof.

6. A compound as claimed in claim 3, and being the 3-(2-piperidinopropyl)-4-(4-methoxyphenyl)-1,5,6,7-tetrahydro-2H-azepinone, or a therapeutically useful acid addition salt thereof.

7. A diuretic or antihypertensive pharmaceutical composition comprising a diuretically or antihypertensively effective amount of a compound as claimed in claim 1, together with a pharmaceutical excipient.

8. A method of treating edematous or hypertensive conditions in a mammal, which comprises the enteral or parenteral administration to said mammal of a composition as claimed in claim 7.

* * * * *